United States Patent [19]

Shiba et al.

[11] Patent Number: 4,659,437

[45] Date of Patent: Apr. 21, 1987

[54] METHOD OF THERMAL DIFFUSION ALLOY PLATING FOR STEEL WIRE ON CONTINUOUS BASIS

[75] Inventors: Takeshi Shiba; Toshiaki Shimizu; Fumihiro Yanase, all of Ono, Japan

[73] Assignee: Tokusen Kogyo Kabushiki Kaisha, Hyogo, Japan

[21] Appl. No.: 688,841

[22] Filed: Jan. 4, 1985

[51] Int. Cl.$^4$ .......................... C25D 7/06; C25D 5/50
[52] U.S. Cl. ...................................... 204/28; 204/37.1
[58] Field of Search .................. 204/27, 28, 37.1, 1 T, 204/43.1

[56] References Cited

U.S. PATENT DOCUMENTS

| | | | |
|---|---|---|---|
| 3,772,174 | 11/1973 | Spalvins | 204/192 |
| 4,367,125 | 1/1983 | Avellone | 204/28 |
| 4,545,834 | 10/1985 | Shemenski et al. | 156/124 |

Primary Examiner—John F. Niebling
Assistant Examiner—William T. Leader
Attorney, Agent, or Firm—Wenderoth, Lind & Ponack

[57] ABSTRACT

A method of thermal diffusion alloy plating for steel wire including the steps of continuously detecting the quantity of metal plated, plated metal composition, plating composition gradient or combination thereof, in thermal diffusion alloy plating effected continuously on steel wire. Detection of these valves is performed by an energy dispersive type X-ray fluorescent analyzer and upon detecting any variation in these values, a control signal is given to a control unit to adjust automatically the plating electric current and the diffusion heating quantity, thereby imparting the desired quantity of metal plated, the desired plated alloy composition ratio and the desired plating composition gradient uniformly in the lengthwise direction of steel wire.

6 Claims, 17 Drawing Figures

FIG.6(a)
FIG.6(b)
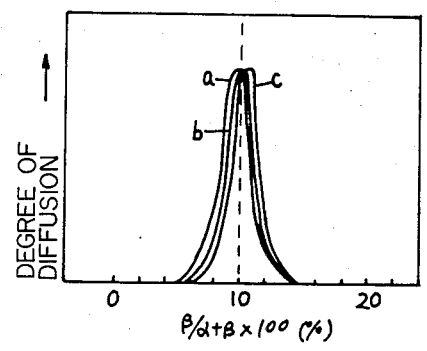
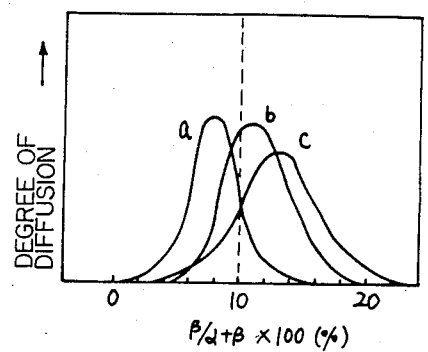
FIG.7
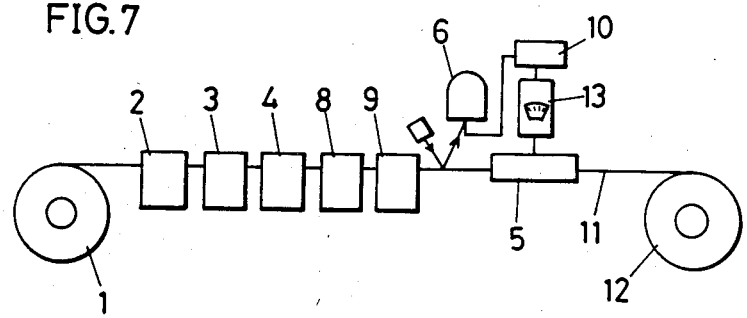
FIG.8
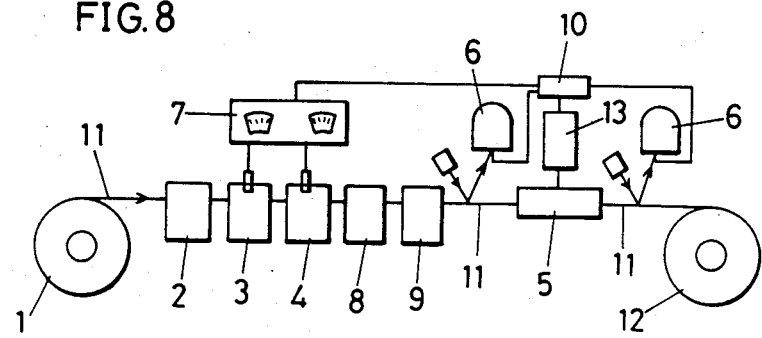

METHOD OF THERMAL DIFFUSION ALLOY PLATING FOR STEEL WIRE ON CONTINUOUS BASIS

BACKGROUND OF THE INVENTION

1. Field of the Invention

This invention relates to a method of thermal diffusion alloy plating for steel wire on a continuous basis, comprising the steps of plating steel wire with at least two different kinds of metal continuously in at least two layers of different metal and effecting thermal diffusion alloy plating on the steel wire plated in layers.

2. Prior Art

Conventionally, in the case where alloy plating is effected on steel wire with at least two different kinds of metal continuously, firstly steel wire is plated with different metals in layers in turn and then a thermal diffusion treatment is given to the plated steel wire for alloy plating.

The above method, however, causes irregularity in the quantity of metal plated, the plated alloy composition ratio (ratio of various metals composing the alloy plating in weight (%)) of plating composition gradient (degree of change of alloy composition ratio from the inner part to the outer part of alloy plating), etc. due to the changes in plating electric current efficiency (caused by changes in concentration of plating liquid, changes in plating voltage, wear of electrode poles, condition of an electrode plate, etc.), changes in diffusion voltage, changes in electric current, etc. Thus, it is very difficult to obtain the desired alloy plating with good precision and with uniformity in the lengthwise direction of the steel wire.

Especially in the case of steel wire to be used for reinforcing the rubber of tires for motor vehicles, conveyors, etc., strength and adhesion to rubber are essential to the steel wire and strict precision is required for alloy plating of this kind. More particularly, alloy plating for the steel wire is strictly limited in the quantity of metal plated and plated alloy composition ratio (ratio of Cu to Zn in weight, for example) for the aspect of adhesion to rubber and their value varies delicately according to the kind of rubber.

It is a fact that in order to improve adhesiveness, it is required to make changes between the inner part (central side) and at the outer part (outer circumferential side) and also to give an appropriate gradient to the composition ratio (composition gradient) from the inner to the outer side of the plating.

The quantity of metal plated, plated alloy composition ratio and the plating composition gradient affect rubber more or less and their effect on even one and the same rubber varies according to the condition under which the rubber is used. For example, in the case where rubber is used under a condition of high temperature, it is affected largely by the plated alloy composition ratio and in a wet condition, it is affected largely by the composition ratio. Therefore, it is necessary to take into consideration the combination of values of the quantity of metal plated, the plated alloy composition ratio and the plating composition inclination according to the kind, use, etc. of the rubber.

The precision required for alloy plating affects to a large extent the drawability in a drawing process which is carried out after alloy plating. Especially, the plated alloy composition ratio is related to breakage of wire in a drawing process.

A conventional method of alloy plating aiming at the desired quantity of metal plated, plated alloy composition ratio or plating composition gradient in good precision and in uniformity in the lengthwise direction of steel wire includes such steps that a thermal diffusion alloy plated steel wire is sampled for the purpose of analysis, and various analyses, including a fluorescence X-ray analysis and analysis performed by the atomic absorption method, are carried out with the sample and on the basis of analytical results obtained, a plating electric current value in each plating tank for various metal plating is adjusted to obtain alloy plating having the desired quantity of metal plated and the desired plating alloy composition ratio.

Other methods available are, for example, the method of raising a temperature by Joules heat generation by electrifying steel wire directly, based on the idea that for obtaining the desired plating composition gradient uniformly, the diffusion temperature of steel wire is maintained at a fixed level by giving the prescribed heat value to the steel wire, and the method of indirect heating by making steel wire pass through a diffusion furnace. However, these methods have such a defect that even if the prescribed heat value is given for obtaining the desired plating composition gradient, the temperature of the steel wire itself does not always rise to the desired degree or such a defect that the composition gradient varies to a large extent due to a change in heating quantity, a change in the time of maintaining the raised temperature and a change in the thickness of the layer of each metal composing the alloy and the ratio of metals in weight.

For obtaining a steel wire of uniform alloy plating precision on a continuous basis by the above methods, it is suggested to carry out as frequent sampling and analyzing as possible, but since continuity is required for steel wire, this suggestion is not practicable.

Even if we try to manufacture brass plated steel wire of Cu conc. 65% by the above conventional methods, it is the utmost we can to limit the range within 62%–68% and therefore it is inevitable that we have irregularity of ±3% in the Cu concentration.

The relation between Cu concentration (Cu/Cu+Zn×100 (ratio in weight)) and adhesiveness to rubber and that between Cu concentration and drawability are as shown in FIG. 12(a). "Rubber adhering after adhesion test" in this figure represents the quantity of rubber adhered to the surface of steel wire which was left for two weeks at 80° C.×95% RH after it was plated with brass by thermal diffusion and subjected to a drawing process. The relation between the diffusion heating quantity obtained under the fixed Cu concentration and adhesiveness to rubber and that between the diffusion heating quantity and the drawability are as shown in FIG. 12(b). "Adhering of rubber after adhesion test" in this figure represents the quantity of rubber adhered to the surface of steel wire which was left for two weeks at 80° C.×95% RH after it was plated with brass at Cu conc. 65% and subjected to a drawing process.

As is obvious from FIGS. 12(a) and 12(b), adhesiveness to rubber and drawability have a reciprocal relation with each other. The fact that the irregularity of ±3% is inevitable in the conventional method is one of the reasons why steel wire of good alloy plating precision cannot be manufactured by the conventional method. It is therefore an important problem of the moment to lessen the irregularity in Cu concentration in the method of thermal diffusion alloy plating for steel wire by controlling the quantity of metal plated, plated alloy composition ratio and plating composition gradient.

SUMMARY OF THE INVENTION

The present invention has for its object to provide a method of thermal diffusion alloy plating for steel wire, comprising the steps of detecting at every moment the quantity of metal plated, the plated metal composition, the plating composition gradient or combination thereof in a thermal diffusion alloy plating effected continuously on steel wire by the energy dispersive X-ray spectrometer type X-ray fluorescence analyzer and upon detecting any variation in these values, a control signal is given to a control unit to adjust automatically the plating electric current and the diffusion heating quantity in the plating diffusion process, thereby imparting the desired quantity of metal plated, the desired plated alloy composition ratio and the desired plating composition gradient uniformly in the lengthwise direction of steel wire.

BRIEF DESCRIPTION OF THE DRAWINGS

The nature and advantage of the present invention will be understood more clearly from the following description of preferred embodiments of the present invention and the accompanying drawings, in which:

FIG. 6(a) is a correlation drawing showing the variations of quantity of thermal diffusion of a representative plated lot in Embodiment 2;

FIG. 6(b) is a correlation drawing showing the variations in the quantity of thermal diffusion of a representative plated lot according to a conventional method;

FIG. 7 is a schematic drawing of a manufacturing process of Embodiment 3;

FIG. 8 is a manufacturing process of Embodiment 4;

DETAILED DESCRIPTION OF THE PREFERRED EMBODIMENTS

Embodiment 1

Figure 1:
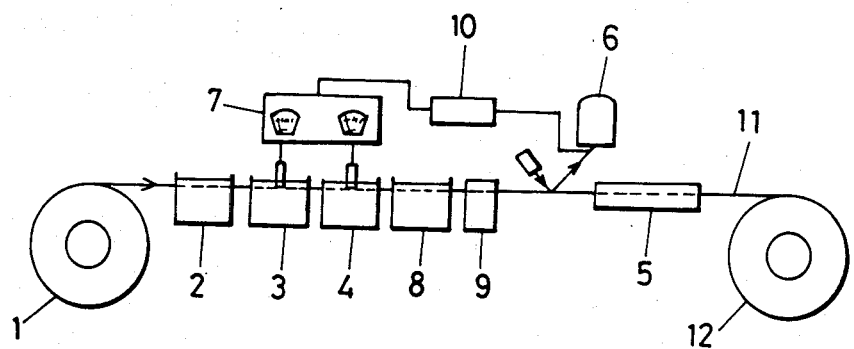
FIG. 1 is a schematic drawing of a manufacturing process of Embodiment 1.

As shown in FIG. 1, steel wire 11 drawn out of a reel 1 passes through a pretreating apparatus 2 (for removing of fat, rinsing, acid scouring, etc.), a first layer metal plating apparatus 3 and a second layer plating apparatus 4, whereby two-layer plating is effected. Then, downrun thereof the two-layer plated steel wire is given an after-treatment by a rinsing apparatus 8 and a drying apparatus 9, and further downrun passes through a thermal diffusing apparatus 5, where it is given a thermal diffusing treatment, and is made into an alloy plated steel wire, which is taken up continuously by a take-up reel 12.

In the thermal diffusion alloy plating process as mentioned above, an energy dispersive X-ray spectrometer type X-ray fluorescence analyzer 6 or EDX (including an X-ray fluorescence tube and an analyzing part) is arranged next to the drying apparatus 9, X-rays from the fluorescence tube are applied to the surface of the steel wire 11 and characteristic X-rays from each metal plated in two layers on the surface of the steel wire 11 are detected simultaneously by the analyzing part of the analyzer 6. By the variation of the ratio of the strengths of the X-rays emitted from each of the two different metals to the same thereof (hereinafter "the strength ratio"), changes in the quantity of metal plated and the ratio of metals in weight are sensed. If any variation is sensed, a control signal is sent to an electric current control apparatus 7 via a microcomputer 10 so that the ratio of characteristic X-rays strength may be kept constant. Thus, plating electric current of the metal plating apparatuses 3, 4 is automatically controlled so that the desired quantity of metal plated and the desired ratio of metals in weight can be obtained uniformly in the lengthwise direction of steel wire.

In this embodiment, the quantity of metal plated of a plated layer and the ratio of each metal are measured in the state of layer before thermal diffusion and without stopping operation. Measured values are fed back to each plating process for adjusting of plating electric current and thus alloy plated steel wire of good precision can be obtained continuously.

An explanation is given below about the case where brass plating was effected on steel wire.

In the case where measuring is made in the state of linear body by an EDX, several kinds of brass plated steel wire whose quantity of metal plated and alloy composition are already known are measured and the following ratio of secondary X-ray strength from Cu and Zn in brass plating and from Fe (steel wire) is obtained, namely, In thickness, ICu/IFe+IZn/IFe is measured where:

ICu: Secondary X-ray strength from Cu (cps)

IZn: Secondary X-ray strength from Zn (cps)

IFe: Secondary X-ray strength from Fe (cps)

(cps)—Count per second

In composition ratio,

ICu/(ICu+IZn) is measured.

Figure 2A:
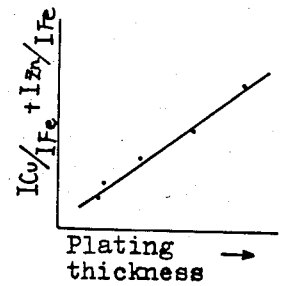
FIGS. 2(a) and 2(b) are correlation drawings showing the working curve of fluorescence X-ray analysis in brass plating on Fe.
Figure 2B:
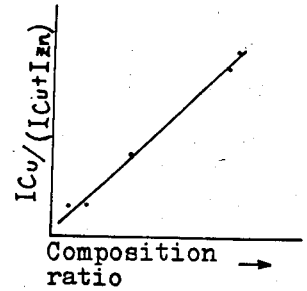

Working curves as shown in FIG. 2(a) and FIG. 2(b) are prepared from the above ratios and from the actual quantity of metal plated and the composition ratio. On the basis of these working curves, the thickness of plating and the composition ratio (Cu concentration in this case) are known from each secondary X-ray strength obtained by measuring the unknown samples.

Figure 3A:
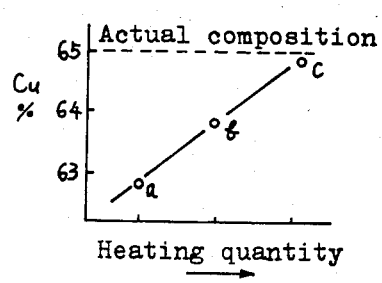
FIG. 3(a) is a correlation drawing showing the result of fluorescence X-ray analysis by heating quantity in thermal diffusion brass plating on steel wire.
Figure 3B:
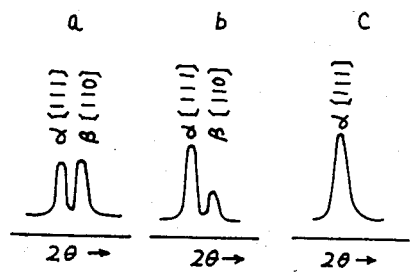
FIG. 3(b) is a X-ray analysis drawing showing the change of alloyed state in each plating.

However, in actual thermal diffusion brass plated wire, when a difference in composition ratio (ratio of Cu to Zn) took place between the inner part and the outer part of plating, secondary X-ray generated from the inner part of the plating or from steel wire involves an error in measured value, different from the case of uniformly brass plated steel wire. FIGS. 3a and 3b show an example of the composition ratio in the case of fluorescence X-ray analysis (using a working curve obtained from a standard sample of uniform thickness) of steel wire plated with Cu at the first layer and Zn at the second layer and subjected to varying degree of thermal diffusion a, b and c. FIG. 3(b) shows the difference in $\alpha$-phase and $\beta$-phase measured by the EDX at the different levels of thermal diffusion a, b, and c.

In this embodiment, in order to avoid a measuring error which is caused by such variations in state the state of diffusion, the working curve was prepared from the quantity of each metal plated in a layer before thermal diffusion with samples whose metal ratio is known, and on the basis of the working curve unknown samples were measured before thermal diffusion during actual continuous operation. In this way, measuring error is avoided.

Figure 4A:
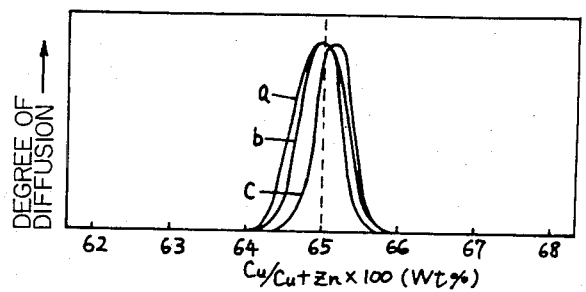
FIGS. 4(a) and 4(b) are respectively correlation drawings showing the variations of composition of a representative plating production lot by the process of embodiment 1 and by the conventional method.
Figure 4B:
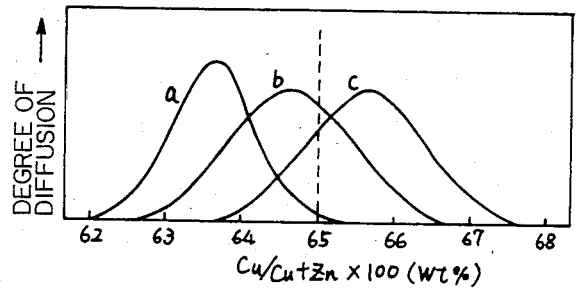

FIG. 4(a) and FIG. 4(b) show the state of distribution of plating composition of a representative plating production lot in the case where brass plated steel wire of Cu concentration 65% was manufactured respectively by the method of this embodiment and by the conventional method, for the different levels of thermal diffusion a, b, and c. As is obvious from these figures, while the irregularity of a little more than ±3% is shown for the conventional method, the irregularity of a little less than ±1% is shown for the method of this embodiment.

Embodiment 2

Figure 5:
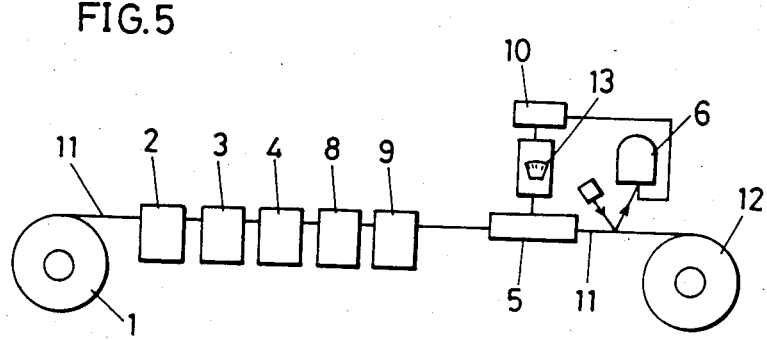
FIG. 5 is a schematic drawing of a manufacturing process of Embodiment 2.

FIG. 5 shows Embodiment 2. In the thermal diffusion alloy plating process of Embodiment 2, which is similar to Embodiment 1, an EDX 6 is arranged near the steel wire at the back of the thermal diffusing apparatus 5.

According to this embodiment, characteristic X-ray from each metal of alloy plated component which covers the surface of steel wire 11 is detected simultaneously by the EDX 6 and variations of the degree of diffusion of alloyed plating are analyzed and sensed by variations of the strength ratio and values of variation thus sensed, are transferred to a thermal diffusion control apparatus 13 via the microcomputer 10, whereby diffusion heat value of the thermal diffusing apparatus 5 is automatically controlled so that the desired degree of diffusion can be obtained uniformly in the lengthwise direction of the steel wire.

The method of detecting simultaneously characteristic X-rays of each metal of plating components which were alloyed, by the EDX 6 and judging the degree of diffusion from each ratio, utilizes the phenomenon that characteristic X-rays generated from each metal of the alloy plating are absorbed by the other metal and the degree of such absorption varies with the degree of diffusion.

If sufficient heat value is imparted to metal plated in two layers, the composition ratio of each metal of the alloy plating is uniform at the inner part and the outer part (perfect degree of diffusion) but if less heat value is imparted, the alloy composition ratio at the inner part and the outer part of the plating has a gradient (imperfect diffusion). In this case, however, the metal which is at the second layer in two-layer plating before diffusion, namely, metal plated at the outer side shows a high ratio at the outer side of plating and the metal plated at the first layer, namely, at the inner side, shows a high ratio at the inner side. In the course of diffusion by heating two-layer plating on steel wire, the ratio of metal at the second layer before diffusion existing at the outer side of plating decreases gradually and finally such ratio becomes uniform at the inner part and the outer part of plating. In the case where characteristic X-rays from each metal of plating in such course is detected by the EDX, the rate at which characteristic X-rays from metal at the first layer is absorbed by metal at the second layer decreases gradually. In other words, in the two-layer state before diffusion, absorption becomes the maximum, but in the state of perfect diffusion absorption becomes the minimum. Therefore, the strength ratio of characteristic X-rays from the two layers to be obtained by fluorescence X-ray varies with the degree of diffusion before diffusion and after alloying, although the total quantity of two-layer metal in plating existing on steel wire does not change. In other words, with the progress of the degree of diffusion, the strength of characteristic X-rays from metal plated at the first layer increases but on the contrary, strength of characteristic X-ray from metal plated at the second layer decreases.

In this embodiment, the degree of diffusion is judged by utilizing the relation between the degree of diffusion and the strength ratio of characteristic X-rays, that is, the correlation between the degree of diffusion and the ratio of the strength of the characteristic X-rays emitted by the metal plated at the inner layer to that plated at both layers. In the case of brass plating, the characteristic X-rays for copper are reflected by the $\beta$-phase (III) of brass and the characteristic X-rays for zinc are reflected by the $\alpha$-phase (110), and the applicable ratio is $\beta/(\alpha+\beta)$. In the steel wire plated in a two-layer state aiming at the required alloy ratio, if samples for which the degree of diffusion were varied gradually are prepared beforehand, and indicating the correlation between data characteristic X-ray strength ratio of metals of the plating component and the degree of defusion therein for such samples are obtained and such data are input to a microcomputer, then the use of EDX 6 in a continuous thermal diffusion alloy plating process makes it possible to judge the degree of diffusion from the characteristic X-ray strength ratio for steel wire plated at the same alloy composition ratio as that of the samples. Thus, it will be possible to adjust automatically the thermal diffusion quantity to the desired degree of diffusion via a microcomputer.

The distribution of diffusion state of alloy plating in manufacturing brass plated steel wire by Embodiment 2 and by the conventional method is shown in FIG. 6(a) and FIG. 6(b). In these figures, $\alpha$ is the height of the peak of $\alpha$ phase (111) of brass measured by the X-ray analyzer and $\beta$ is the height of the peak of $\beta$ phase (110) of brass measured similarly. $\alpha/\alpha+\beta\times100$
is a parameter of the degree of diffusion.

As is obvious from these figures, irregularity of ±7-9% is shown in the desired parameter in the conventional method but the irregularity of a little less than ±4% is apparent in the case of this embodiment.

Embodiment 3

FIG. 7 shows Embodiment 3. In a thermal diffusion alloy plating process similar to Embodiment 1, the EDX 6 is arranged next to the drying apparatus 9, which is connected to the thermal diffusion controlling apparatus 13 via the microcomputer 10.

In the case where variations took place in the plating composition ratio itself during a continuous manufacturing process, namely, variations took place in the quantity of each metal plated before steel wire plated in two layers reaches the thermal diffusion apparatus 5, there is a possibility that the relation between the degree of diffusion and the characteristic X-ray strength ratio as mentioned in Embodiment 2 becomes improper due to the change in the quantity of existing metal. However, basically the characteristic X-ray strength ratio will vary relatively to the variation of the whole metal composition ratio.

In order to eliminate the above trouble, it is proposed, as shown in FIG. 7, to arrange the EDX 6 between the plating process and the thermal diffusing process, to obtain each characteristic X-ray of plating metal in the state of two layers, to correct variation values of characteristic X-ray through the medium of the microcomputer 10 and to transfer the corrected data to the thermal heat value controlling apparatus 13 in the form of control signals so as to control diffusion heat value and thereby obtain the desired degree of diffusion.

Embodiment 4

FIG. 8 shows Embodiment 4. In the thermal diffusion alloy plating process similar to Embodiment 1, first and second EDX's 6 are respectively arranged near the steel wire at the back of the drying apparatus 9 and near the steel wire at the back of the thermal diffusion apparatus 5. Both of the analyzers 6 are connected to the electric current controlling apparatus 7 and the diffusion heat value controlling apparatus 13.

According to this embodiment, in the case where variations have taken place in the quantity of metal plated and in the degree of diffusion of alloy plating during the continuous manufacturing process, variation values obtained by the EDX's 6 are corrected at any time through the medium of the microcomputer 10 and corrected data are converted into control signals, which are transferred to the electric current controlling apparatus 7 and the diffusion heat value controlling apparatus 13 to obtain alloy plating of good precision, free from irregularities of the quantity of metal plated, plating alloy composition ratio and plating composition gradient, in the lengthwise direction of steel wire.

Each of the above embodiments refer to the method of alloy plating with two different metals but alloy plating with three or more different metals can be effected in the same way because in the method of effecting thermal diffusion after plating in multilayer, there is caused difference in composition ratio at the inner part and the outer part of plating according to the degree of diffusion and therefore processing can be carried out in the same way as in the case of two-layer plating.

As the fluorescence X-ray analyzer to be used for the present invention, a wavelength dispersive type can be used in addition to an energy dispersive type. However, since it is necessary to detect at least two kinds of characteristic X-rays simultaneously from the same place, the wavelength dispersive type requires spectro-crystals and detecters in the number corresponding to the number of plating component metals. Also, there is a geographical limit in the position of installation for the wavelength dispersive type. On the other hand, the energy dispersive type can detect simultaneously, characteristic X-rays in the whole energy range and there is only slight limit in the position of installation for the energy dispersive type. Therefore, the energy dispersive type is more effective for a linear body such as a steel wire. Moreover, use of the energy dispersive type makes it possible to carry out a precise analysis even in continuous manufacturing of fine linear body of 1 m.m. in diameter which involves microscopic vibration. Characteristic X-rays to be detected can be of any energy level of the Ka line and La line but from the aspect of absorption, proper selection should be made according to the quantity of metal plated, alloy plating components, etc.

Figure 9:
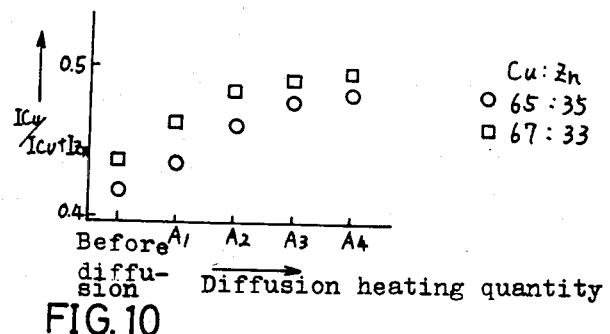
FIG. 9 is a correlation drawing showing the correlation between the diffusion heating quantity and the characteristic X-ray strength.
Figure 10:
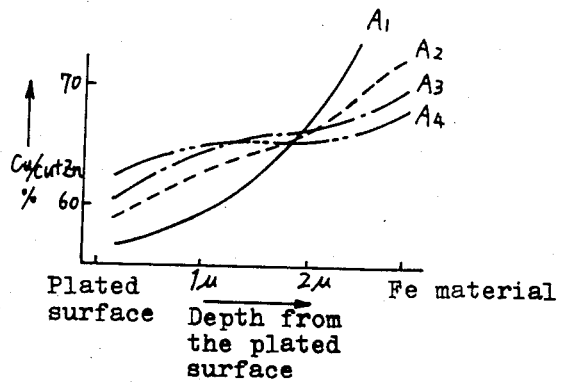
FIG. 10 is a curve drawing showing the composition gradient at the inner part and the outer part of plating.
Figure 11:
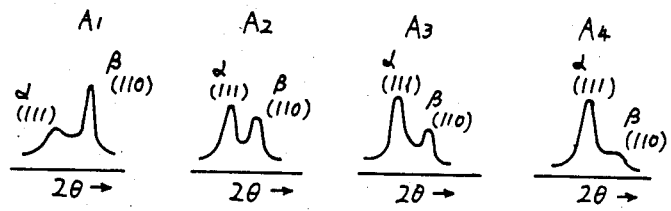
FIG. 11 is an X-ray analysis drawing showing the change in the degree of diffusion and alloyed state.
Figure 12A:
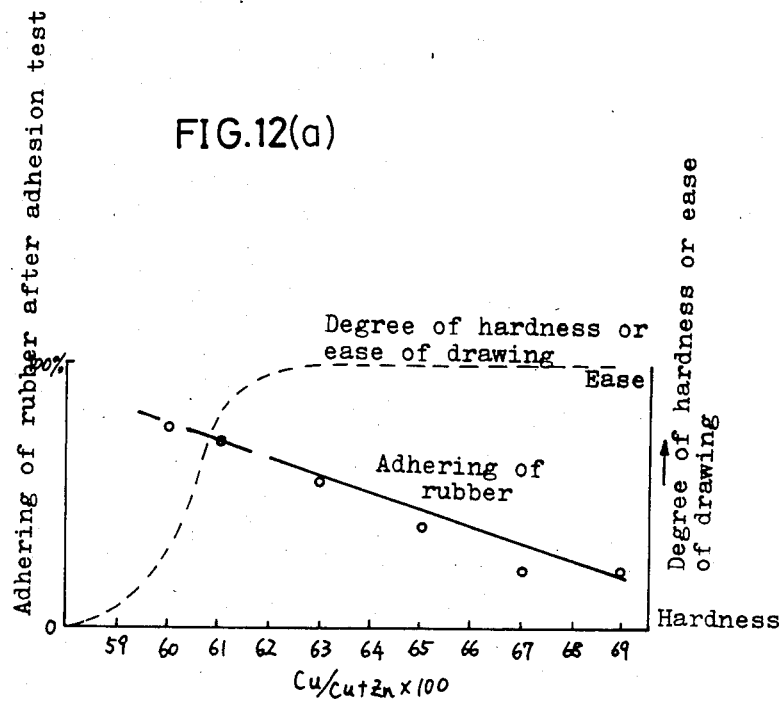
FIG. 12(a) is a correlation drawing showing the correlation between the Cu concentration and the adhesiveness to rubber and between the Cu concentration and the drawability.
Figure 12B:
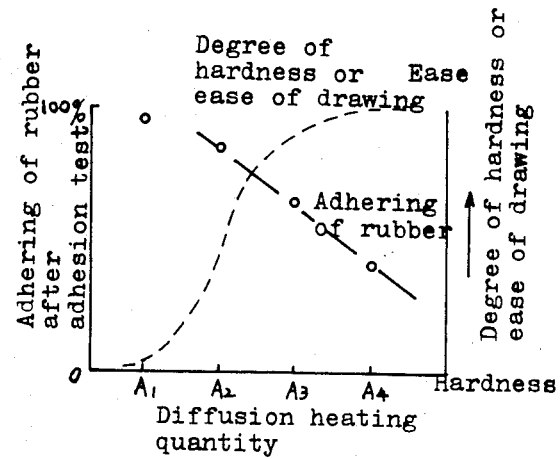
FIG. 12(b) is a correlation drawing showing the correlation between the diffusion heating quantity and the adhesiveness to rubber and between the diffusion heating quantity and the drawability.

FIG. 9 is a relation drawing showing the correlation between the characteristic X-ray strength ratio to the diffusion heating quantity of thermal diffusion brass plated steel wire to be used for steel cord of motor vehicles. In order to have the composition ratio of Cu and Zn at 65%:35% and at 67%:33%, the diffusion heating quantity applied to the steel wire having Cu plating at the first layer and Zn plating at the second layer was varied among heating quantitites A1, A2, A3 and A4. It is indicated that with the increase of heating quantity, characteristic X-ray strength ratio from Cu plated at the first layer increases. FIG. 10 and FIG. 11 show the state of the alloy of the same sample measured by the EDX. These figures indicate that if the thermal diffusion quantity is so controlled that the characteristic X-ray strength ratio of Cu and Zn to correspond to the desired degree of diffusion is kept constant, steel wire for tire cord can be manufactured continuously without any variation.

According to the method of the present invention, variations of the quantity of metal plated and the alloy plating composition ratio of a linear body during continuous manufacturing are analyzed and corrected by the EDX and the microcomputer and such corrected data are transferred to a control unit for automatic adjusting of plating electric current and diffusion heating quantity. Therefore, irregularities of the quantity of metal plated, alloy plating composition ratio and plating composition gradient are only slight and alloy plating of good precision in plating composition gradient can be effected uniformly in the lengthwise direction of a linear body. Also, the method according to the present invention is most suitable for manufacturing of steel wire for tire cords of motor vehicles for which strict precision is required in the quantity of metal plated, plating alloy composition ratio and plating composition gradient from the aspect of adhesiveness to rubber and drawability.

We claim:

1. In a method of continuously alloy plating steel wire with at least two different kinds of metal, the method including the step of continuously plating respective layers of each metal onto running steel wire with electrical plating currents of a plating apparatus, and the step of continuously subjecting the plated layers to thermal diffusion with a thermal diffusing apparatus, downrun of the plating apparatus during the step of continuously plating to form an alloy plating on the running steel wire, the improvement including the steps of:

during the step of plating and the step of subjecting the plated layers to thermal diffusion, continuously directing X-rays against, and measuring characteristic X-rays of, the metals plated on the steel wire, prior to the thermal diffusion thereof, with an energy dispersive type X-ray fluorescence analyzer which includes an X-ray fluorescence tube and an analyzing part, producing variation value signals in the analyzer related to the measured characteristic X-rays, indicative of the variations along the length of the wire of the quantities of the respective metals plated onto the steel wire during the step of continuously plating, and producing control signals related to the variation value signals and controlling the electrical plating currents with the control signals.

2. In the improved method as in claim 1, the improvement wherein the step of producing control signals includes the step of transmitting the variation value signals to a microcomputer and producing the control signals in the microcomputer.

3. In a method of continuously alloy plating steel wire with at least two different kinds of metals, the method including the step of continuously plating respective layers of each metal onto running steel wire with electrical plating currents of a plating apparatus, and the step of continuously subjecting the plated layers to thermal diffusion by applying heat thereto with a thermal diffusing apparatus, downrun of the plating apparatus during the step of continously plating to form an alloy plating on the running steel wire, the improvement including the steps of:

during the step of plating and the step of subjecting the plated layers to thermal diffusion, continuously directing X-rays against, and measuring characteristic X-rays of, the metals of the alloy plating plated on the steel wire, after the thermal diffusion thereof, with an energy dispersive type X-ray fluorescence analyzer which includes an X-ray fluorescence tube and an analyzing part, producing a variation value signal in the analyzer related to the measured characteristic X-rays, indicative of the variations along the length of the wire of the degree of diffusion of the metals in the alloy during the step of continuously subjecting the plated layers to thermal diffusion, and producing a control signal related to the variation value signal and controlling the quantity of heat applied to the plated layers by the thermal diffusing apparatus with the control signal.

4. In the improved method as in claim 3, the improvement wherein the step of producing a control signal includes the step of transmitting the variation value signal to a microcomputer and producing the control signal in the microcomputer.

5. In a method of continuously alloy plating steel wire with at least two different kinds of metal, the method including the step of continuously plating respective layers of each metal onto running steel wire with electrical plating currents of a plating apparatus, and the step of continuously subjecting the plated layers to thermal diffusion by applying heat thereto with a thermal diffusing apparatus, downrun of the plating apparatus during the step of continuously plating to form an alloy plating on the running steel wire, the improvement including the steps of:

during the step of plating and the step of subjecting the plated layers to thermal diffusion, continuously directing X-rays against, and measuring first characteristic X-rays of, the metals plated on the steel wire, prior to the thermal diffusion thereof, with a first energy dispersive type X-ray fluorescence analyzer which includes a first X-ray fluorescence tube and a first analyzing part, producing first variation value signals in the first analyzer related to the measured first characteristic X-rays, indicative of the variations along the length of the wire of the quantities of the respective metals plated onto the steel wire during the step of continuously plating, producing first control signals related to the first variations value signals and controlling the electrical plating currents with the first control signals, during the step of plating and the step of subjecting the plated layers to thermal diffusion, continuously directing X-rays against, and measuring second characteristic X-rays of, the metals of the alloy plating plated on the steel wire, after the thermal diffusion thereof, with a second energy dispersive type X-ray fluorescence analyzer which includes a second X-ray fluorescence tube and a second analyzing part, producing a second variation value signal in the second analyzer related to the measured second characteristic X-rays, indicative of the variations along the length of the wire of diffusion of the metals in the alloy during the step of continuously subjecting the plated layers to thermal diffusion, and producing a second control signal related to the second variation value signal and controlling the quantity of heat applied to the plated layers by the thermal diffusing apparatus with the second control signal.

6. In the improved method as in claim 5, the improvement wherein the step of producing a control signal includes the step of transmitting the variation value signal to a microcomputer and producing the control signal in the microcomputer.

* * * * *